United States Patent [19]

Collins

[11] Patent Number: 4,726,808
[45] Date of Patent: Feb. 23, 1988

[54] MANDIBULAR PROSTHESIS

[76] Inventor: Thomas A. Collins, R.F.D. 8, Springfield, Mo. 65804

[21] Appl. No.: 879,964

[22] Filed: Jun. 30, 1986

[51] Int. Cl.[4] .............................................. A61F 2/28
[52] U.S. Cl. ................................................... 623/16
[58] Field of Search ..................... 623/16, 18; 128/922; 433/176, 173

[56] References Cited

U.S. PATENT DOCUMENTS

| D. 288,236 | 2/1987 | Homsy | 623/16 |
| 3,720,959 | 3/1973 | Hahn | 623/16 |
| 3,900,025 | 8/1975 | Barnes | 128/92 R |

Primary Examiner—Richard J. Apley
Assistant Examiner—James Prizant
Attorney, Agent, or Firm—Kokjer, Kircher, Bradley, Wharton, Bowman & Johnson

[57] ABSTRACT

A mandibular prosthesis includes a pair of strips joined at one end and spaced apart elsewhere for placement on opposite sides of a mandibular stump. The strips each have alternating threaded and non-threaded holes that are aligned with respective non-threaded and threaded holes in the other strip. Consequently, screws can be applied from either side and the prosthesis can be implanted interchangeably on either side of the mandible. Extending from the joined end of the strips is a mandibular replacement which may be an artificial condyle, a band for replacing the main body of the mandible, or a band carrying additional attachment strips or a ramus and condyle replacement.

13 Claims, 7 Drawing Figures

U.S. Patent  Feb. 23, 1988  4,726,808
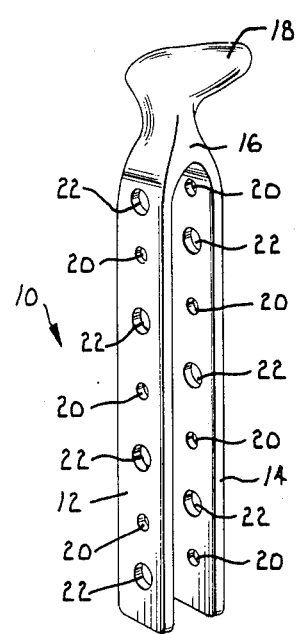
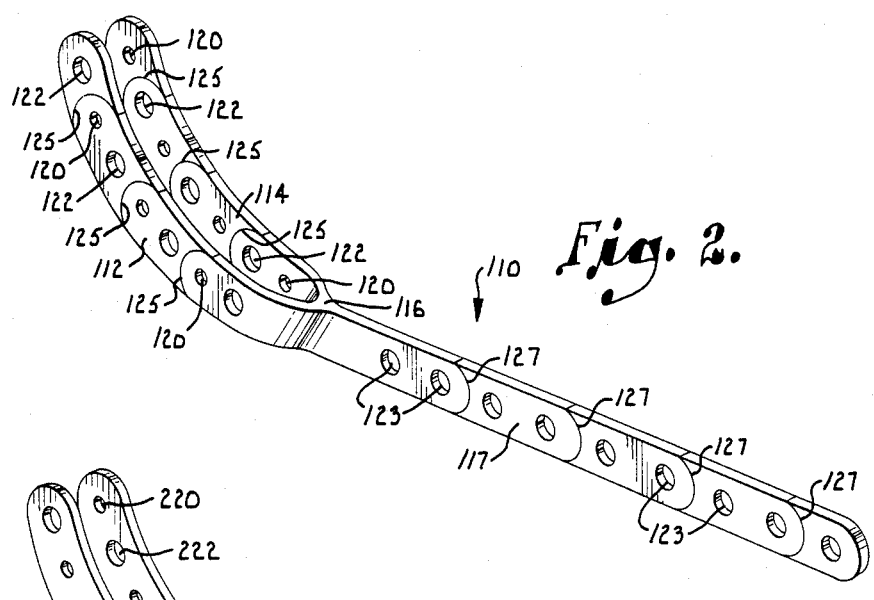
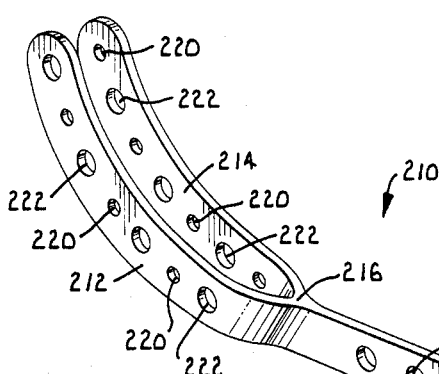
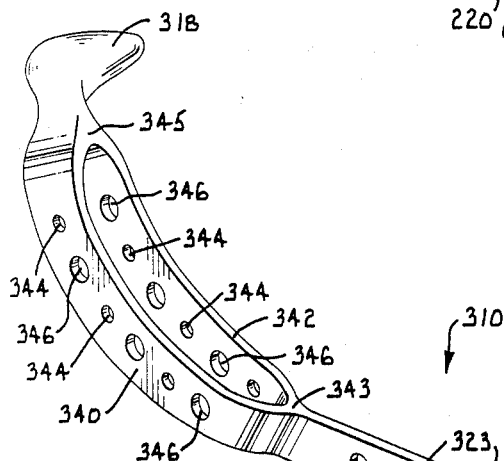
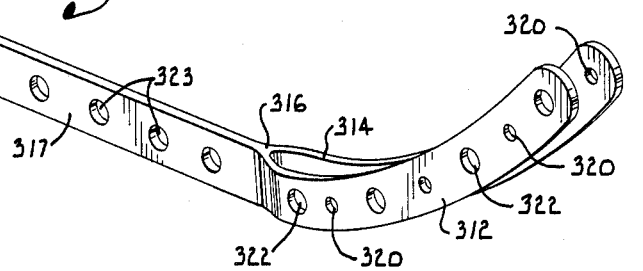

MANDIBULAR PROSTHESIS

BACKGROUND AND SUMMARY OF THE INVENTION

This invention relates in general to prosthetic devices and more particularly to an improved mandibular prosthesis for replacing all or part of a defective or damaged jawbone.

In the past, the mandibular prostheses that have been available have not been altogether satisfactory. Typically, nuts and bolts are used to fasten the prostheses in place on the mandible, and this results in projections which cause discomfort and possible tissue damage in the patient. Slotting of the bone and the use of templates and wrenches are often required. In addition, the nuts tend to work loose in time and thereby detract from the integrity of the implanted structure. Existing mandibular prostheses have also been difficult to surgically implant, primarily because of their bulky nature and the difficulty involved in handling them. Perhaps even more importantly, the fastening systems that have been used are unable to stabilize the implanted structure securely in place. As a consequence, bone grafts are subjected to atrophy and other adverse effects that can in turn create problems in the facial tissues and other nearby tissues.

U.S. Pat. No. 3,720,959 to Hahn discloses a prosthesis that is constructed of malleable mesh material. This device is not only complicated and expensive to manufacture, but it also lacks structural strength and is fastened to the mandible in a less than satisfactory manner. The attachment of a bone graft to the Hahn device is difficult if not impossible.

The present invention is directed to an improved mandibular prosthesis which can be used in the replacement or reconstruction of virtually any part of the mandible. The prosthesis is characterized by a bifurcated structure presenting a pair of metal strips which are placed on opposite sides of a mandibular bone stump that remains on one side of the damaged area of the mandible. The metal strips are provided with alternating threaded and non-threaded holes, and the threaded holes on each strip are aligned with non-threaded holes in the other strip so that screws can be extended between the strips from either side. This makes the prosthesis reversible and allows it to be used on either side of the mandible.

It is an important object of the invention to provide a mandibular prosthesis that can be surgically implanted more quickly and easily than the prostheses that have been available in the past.

Another important object of the invention is to provide a mandibular prosthesis which is improved as to its structural integrity and which is secured in place with greater stability and lateral to medial holding power than is achieved with existing prostheses.

A further object of the invention is to provide a mandibular prosthesis which is constructed in a manner permitting it to be "custom tailored" to replace virtually any part of a damaged mandible.

An additional object of the invention is to provide a mandibular prosthesis that is constructed and fastened in a manner to avoid presenting any projections which can cause significant discomfort or damage to the facial tissue.

Still another object of the invention is to provide a mandibular prosthesis that is reversible so that it can be fitted on either side of the mandible.

Yet another object of the invention is to provide a mandibular prosthesis which is constructed simply and economically and which allows the jaw to function in a normal fashion for an extended period of time.

Other and further objects of the invention, together with the features of novelty appurtenant thereto, will appear in the course of the following description.

DESCRIPTION OF THE DRAWINGS

In the accompanying drawings which form a part of the specification and are to be read in conjunction therewith and in which like reference numerals are used to indicate like parts in the various views:

FIG. 1 is a perspective view of a mandibular prosthesis in a form suitable for replacement of the condyle in accordance with the present invention;

FIG. 2 is a perspective view of a mandibular prosthesis in a form suitable to replace part of the main body of the mandible in accordance with the present invention;

FIG. 3 is a perspective view of another form of the mandibular prosthesis;

FIG. 4 is a perspective view of a mandibular prosthesis in a form suitable for replacing the main body, ramus and condyle in accordance with the present invention;

DETAILED DESCRIPTION OF THE INVENTION

Figure 5:
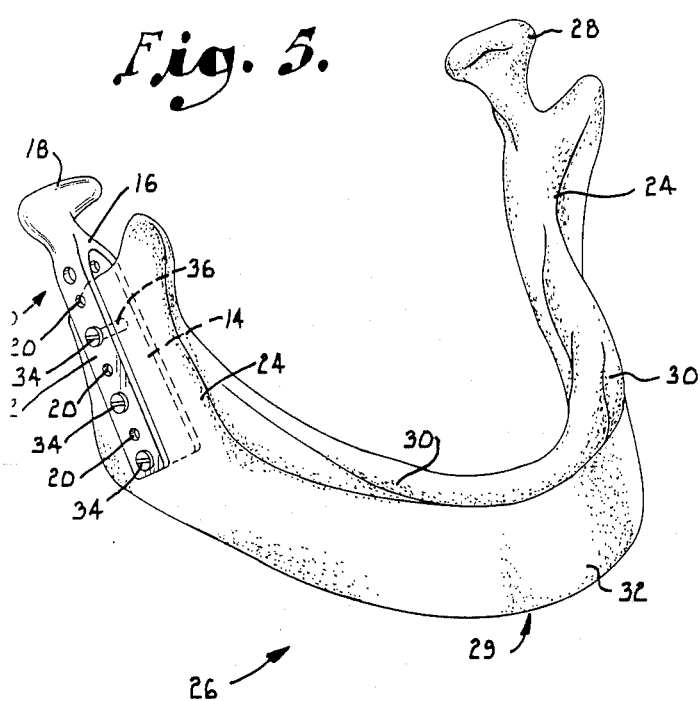
FIG. 5 is a perspective view showing the prosthesis of FIG. 1 applied to replace the condyle.

Referring initially to FIG. 1, numeral 10 generally designates a mandibular prosthesis which is constructed to be implanted on the mandible as a replacement for a damaged or destroyed condyle. The prosthesis 10 includes a pair of metal strips 12 and 14 which are joined at one end 16 and spaced apart as they extend away from end 16. Attached to the joined end 16 of the strips 12 and 14 is an artificial condyle 18.

Each of the strips 12 and 14 is provided with a row of spaced apart openings. Each row of openings includes a plurality of threaded openings 20 which are arranged in an alternating pattern with a plurality of non-threaded openings 22. The non-threaded openings 22 are larger than the threaded openings 20. Each threaded opening 20 on strip 12 is aligned with an opposing non-threaded opening 22 on strip 14, and each non-threaded opening on strip 12 is similarly aligned with a threaded opening 20 on strip 14.

FIG. 5 illustrates the prosthesis 10 implanted on a ramus 24 which terminates in a stump adjacent to a destroyed condyle. The remaining condyle on the opposite side of the mandible 26 is designated by numeral 28. The mandible 26 also includes a main body 29 having generally straight portions 30 and a curved bow 32 located between the straight portions 30 in the area of the chin.

The prosthesis 10 is attached to the stump of ramus 24 by a plurality of screws 34 each having an externally threaded shank 36. The threaded shank 36 of each screw mates with the internal threads in the threaded openings 20, and the screws 34 are long enough to extend between the two strips 12 and 14.

The prosthesis 10 is surgically implanted by placing it on the end of the right ramus stump with strip 12 in front of the ramus 24 and the other strip 14 behind the ramus. Preferably, the strips 12 and 14 fit snugly against the front and back surfaces of the ramus. The prosthesis 10 is positioned on the ramus with the artificial condyle 18 situated in the normal location of the natural condyle. Then, the screws 34 are applied from the front side of the prosthesis and are extended through the non threaded holes 22 in strip 12, through holes that are drilled through the ramus 24, and are threaded into the threaded holes 20 in strip 14. When each of the screws 34 is tightened, the strips 12 and 14 are drawn firmly against the front and back surfaces of the ramus, and the prosthesis 10 is securely mounted in a stable position with the artificial condyle 18 properly situated to replace the damaged natural condyle.

It is noted that the heads of screws 24 fit closely against strip 12 and that the shanks of the screws do not project significantly behind strip 14. The strips 12 and 14 may initially be formed such that they diverge as they extend away from the joined end 16. The strips can then be bent inwardly somewhat at their free ends in order to conform with the thickness of the particular ramus to which they are applied. Alternatively, the prosthesis 10 can be provided in various sizes, with the strips spaced apart to fit thick, normal, and thin rami.

The provision of the alternating threaded and non-threaded holes 20 and 22 enhances the versatility of the prosthesis 10 in that it makes it equally applicable to the left and right rami. If the prosthesis is to be attached to the left ramus, it is simply reversed such that strip 14 is situated in front of the ramus and strip 12 is situated behind the ramus. The screws 34 are then applied through the non-threaded openings 22 of strip 14 and are threaded into the threaded holes 20 of strip 12.

It is contemplated that a sleeve construced to silicone or any suitable plastic material may be applied to the artificial condyle 18 to function as a temporomandibular joint disc (menisus). The sleeve can be split longitudinally, and its two free edges will fit in mating grooves formed in the neck portion of the condyle 18 where it joins end 16, thus securely holding the sleeve in place while allowing it to perform its intended function.

FIGS. 2 and 3 illustrate modified forms of the invention which are constructed for attachment to the ramus in order to replace a damaged portion of the main body 29 of the mandible. The prosthesis shown in FIG. 2 is generally designated by numeral 110 and includes a pair of metal strips 112 and 114 which are joined at one end 116 and which are spaced apart away from end 116. A metal band 117 extends from end 116 away from strips 112 and 114 and serves to replace a damaged portion of the main body 29 of the mandible. Strips 112 and 114 have alternating threaded openings 120 and non-threaded openings 122 that are aligned in the same manner described in connection with openings 20 and 22. The band 117 is provided with a series of holes 123 for receiving screws (not shown) used to attach a bone graft to the band.

The strips 112 and 114 are curved in order to generally conform with the curvature of the ramus 24. Each strip 112 and 114 is provided with a plurality of spaced apart creases 125 that provide weakened areas along which the strip may be broken away. The creases 125 are aligned with one another on the opposing strips 112 and 114. Thus, each strip can be shortened by breaking it along one of these creases 125. Band 117 has a plurality of similar creases 127 which likewise provide weakened areas along which the band may be broken. This permits the band to be shortened as desired by breaking it along one of the creases.

FIG. 3 illustrates a prostheses 220 which is similar in most respects to prosthesis 110. A pair of strips 212 and 214 are joined at one end 216 and are provided with alternating threaded and non-threaded openings 220 and 222. A flat band 217 extends away from end 216 and is provided with openings 223. Although not shown in FIG. 3, strips 212 and 214 may be provided with creases similar to the creases 125 shown in FIG. 2.

The principal difference between the prostheses shown in FIGS. 2 and 3 is that prosthesis 210 is provided with a pair of strips 240 and 242 on the end of the band remote from end 216. The bands 240 and 242 are joined at one end 243 and are spaced apart as they extend away from ends 243. Each strip 240 and 242 is provided with a row of openings consisting of threaded openings 244 arranged in an alternating pattern with non-threaded openings 246. The threaded openings 244 in strip 240 are each aligned with a non-threaded opening 246 in strip 242, and each non-threaded opening 246 in strip 240 is aligned with a threaded opening 244 in strip 242.

Figure 6:
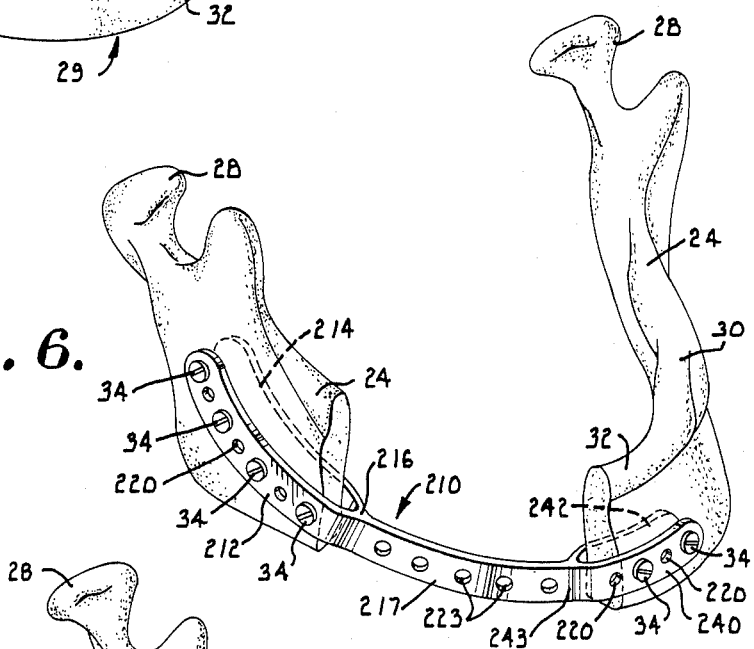
FIG. 6 is a perspective view showing the prosthesis of FIG. 3 attached to the mandible for replacement of part of the main body of the mandible.

Referring now to FIG. 6 in particular, prosthesis 210 is useful in the replacement of part of the main body 29 of the mandible 26. For example, if one of the straight portions 30 is damaged or destroyed, the prosthesis 210 can be implanted in its place. Strips 212 and 214 can be applied on opposite sides of the stump presented at the ramus 24. Screws 34 can be extended through the non-threaded openings 220 in strip 212 and through drilled holes in the ramus 24. The screws are threaded into the threaded openings 220 in strip 214, and tightening of the screws draws the strips 212 and 214 snugly against the front and back surfaces of the ramus.

The other strips 240 and 242 are applied to the stump presented on the bow 32 of the mandible. Strip 240 fits in front of the bow and the other strip 240 fits behind the bow. Screws 34 are extended through the non-threaded openings 246 in strip 240, through holes drilled in the bow 32, and are threaded into the threaded openings 244 in strip 242. When the screws are tightened, strips 240 and 242 are drawn snugly against the front and back surfaces of the bow 32. This completes the surgical implanting of the prosthesis 210. It should be noted that strips 240 and 242 can be bent as necessary to conform with the curvature of bow 32 or any other part of the mandible.

It is also noted that the band 217 can be bent or curved in order to approximate the configuration of the straight portion 30 and the part of the bow 32 which it replaces. In addition, the openings 223 can be used to receive fasteners used to secure a bone graft to the band 217. It should be understood that the band 217 can be long enough to replace substantially the entire main body 29 of the mandible or only a small part of it. If the prosthesis is to replace the entire main body, strips 240 and 242 will have the same curved configuration as strips 212 and 214 in order to conform with the curvature of the ramus 24 on the left side of the mandible. Again, the provision of threaded and non-threaded openings and their alternating arrangement provides the prosthesis 210 with reversibility such that it can be used on either side of the mandible.

It should be understood that the prosthesis 110 shown in FIG. 2 is applied in generally the same manner as prostheses 210. However, prosthesis 110 lacks the fastening strips 240 and 242, and such fastening strips should be bolted or otherwise attached to band 117 after it has been broken to the length necessary to replace the damaged portion of the mandible.

FIG. 4 illustrates yet another modification of the prosthesis which is generally designated by numeral 310. The prosthesis 310 includes a pair of curved strips 312 and 314 which are similar to strips 212 and 214 and which are each provided with alternating threaded holes 320 and non-threaded holes 322. Strips 312 and 314 are joined at one end 316, and a band 317 extends from end 316. Band 317 is provided with a series of openings 323. In the prosthesis 310, strips 240 and 242 are replaced by a pair of curved strips 340 and 342 which are joined at both ends 343 and 345. Band 317 attaches to the strips at end 343, and an artificial condyle 318 extends from end 345. Alternating threaded openings 344 and non threaded openings 346 (aligned in the manner previously described) are provided in a row in each of the strips 340 and 342. Strips 340 and 342 are open between the ends 343 and 345 to receive a bone graft (not shown) that may be used to replace the ramus.

Figure 7:
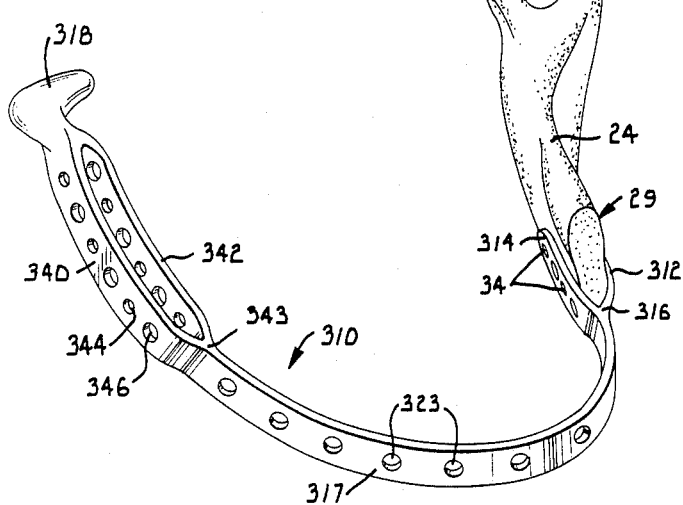
FIG. 7 is a perspective view showing the prosthesis of FIG. 4 attached to a ramus stump to replace a large part of the mandible.

As shown in FIG. 7, prosthesis 310 serves to replace the entire mandible except for one ramus and condyle. Strips 312 and 314 are applied to the stump of the remaining ramus 24 and are drawn snugly against its front and back sides by application and tightening of screws 34. The screws are applied in the manner described previously. Band 317 is bent to conform with the curvature of the damaged main body 29 of the mandible, and the curved strips 340 and 342 act as a replacement for the destroyed right ramus. The destroyed right condyle is replaced by the artificial condyle 318.

The prosthesis 310 is reversible, and the alignment of the threaded and non-threaded openings again allows the screws 34 to be applied from either side in order to accommodate the reversibility of the prosthesis. It should be pointed out that the curved strips 312 and 314 can be replaced with strips like those designated by numerals 240 and 242 in a case where part of the main body 29 remains in place adjacent to the remaining ramus 24.

It is thus evident that the present invention provides a mandibular prosthesis which may be provided in various forms and which can be used to replace virtually any part of a damaged or destroyed mandible. Each form of the prosthesis is mounted to the remaining part of the mandible in a secure and stable manner in order to accommodate bone grafts and provide adequate support for nearby facial tissues. At the same time, the fastening system avoids projections which can cause discomfort and possible damage to the facial tissues.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

Having thus described the invention, I claim:

1. A mandibular prosthesis comprising:
   a pair of strips joined at one end and spaced apart away from said one end for placement on opposite side of a mandibular stump located adjacent a damaged portion of the mandible;
   a mandibular replacement extending from said one end of the strips for replacing the damaged portion of the mandible;
   said mandibular replacement having an artificial condyle;
   a plurality of openings in each strip aligned with openings in the other strip, at least some of said openings being internally threaded; and
   a plurality of externally threaded fasteners for extension between said trips and through the stump to attach said mandibular replacement in a position to replace the damaged portion of the mandible, each fastener having a size and length to pass through an aligned pair of openings and thread into one of the internally threaded openings to maintain said strips against the opposite sides of the stump.

2. The invention of claim 1, wherein said mandibular replacement comprises a metal band adapted to be bent to conform generally in curvature to the curved main body of the mandible.

3. The invention of claim 2, including:
   opposite ends of said band, said strips being connected with one end of the band;
   a second pair of strips on the other end of the band, said strips in the second pair being joined at one end and being spaced apart away from said one end for placement on opposite sides of a second mandible stump spaced from the first mentioned stump; and
   a plurality of openings in each strip in the second pair aligned with openings in the other strip, at least some of the openings being internally threaded to receive the threaded fasteners whereby to attach the strips in said second pair on opposite sides of the second mandible stump.

4. The invention of claim 3, wherein the strips in said second pair are curved for application to the second mandible stump.

5. The invention of claim 4, including a plurality of fastener openings in said band.

6. The invention of claim 1, wherein:
   said openings in each strip are arranged in a row extending lengthwise on the strip;
   each row of openings includes threaded and non-threaded openings arranged in an alternating pattern;
   each threaded opening in one strip is aligned with a non-threaded opening in the other strip; and
   each non-threaded opening in said one strip is aligned with a threaded opening in the other strip, whereby the fasteners can be applied with either strip facing outwardly away from the mandibular stump.

7. The invention of claim 2, including a plurality of creases spaced along the length of said band to provide weakened areas along which the band may be broken for shortening of the band.

8. The invention of claim 7, including a plurality of creases spaced along the length of each strip, said creases on each strip being aligned with the creases on the other strip to provide weakened areas along which each strip may be broken to shorten the strips.

9. The invention of claim 1, including a plurality of creases spaced along the length of each strip, said creases on each strip being aligned with the creases on the other strip to provide weakened areas along which each strip may be broken to shorten the strips.

10. A mandibular prosthesis comprising:
    a bifurcated body having first and second strips joined at one end and spaced apart away from said one end for placement on opposite sides of a mandibular stump located adjacent a damaged portion of the mandible which is to be replaced by the prosthesis, said body further having a mandibular replacement extending from said one end and adapted to replace the damaged portion of the mandible;
    said mandibular replacement having an artificial condyle;
    a row of openings in each strip including alternating threaded and non-threaded openings, each threaded opening in the first strip being aligned with a non-threaded opening in the second strip and each non-threaded opening in the first strip being aligned with a threaded opening in the second strip; and
    a plurality of threaded fasteners each adapted to extend through a non-threaded opening and the mandibular stump and to thread into a threaded opening, whereby the fasteners can be applied from either the side of the body which presents the first strip or the side of the body which presents the second strip to attach the body to the stump with said strips maintained against the opposite sides of the stump.

11. The invention of claim 10, wherein said mandibular replacement comprises a metal band adapted to be bent to conform generally in curvature to the curved main body of the mandible.

12. The invention of claim 11, including:
    opposite ends of said band, said strips being connected with one end of the band;
    a second pair of strips on the other end of the band, said strips in the second pair being joined at one end and being spaced apart away from said one end for placement on opposite sides of a second mandible stump spaced from the first mentioned stump; and
    a plurality of openings in each strip in the second pair aligned with openings in the other strip, at least some of the openings being internally threaded to receive the threaded fasteners whereby to attach the strips in said second pair on opposite sides of the second mandible stump.

13. The invention of claim 10, including a plurality of creases spaced along the length of each strip, said creases on each strip being aligned with the creases on the other strip to provide weakened areas along which each strip may be broken to shorten the strips.

* * * * *